US006402733B1

(12) United States Patent
Daugherty (10) Patent No.: US 6,402,733 B1
(45) Date of Patent: *Jun. 11, 2002

(54) INTRAPULMONARY DELIVERY OF POLYPEPTIDE GROWTH FACTORS AND CYTOKINES

(75) Inventor: Ann L. Daugherty, Palo Alto, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/552,199

(22) Filed: Apr. 19, 2000

Related U.S. Application Data

(63) Continuation of application No. 08/128,058, filed on Sep. 27, 1993, now Pat. No. 6,099,517, which is a continuation of application No. 07/982,268, filed on Nov. 25, 1992, now abandoned, which is a continuation of application No. 07/762,039, filed on Sep. 17, 1991, now abandoned, which is a continuation of application No. 07/312,325, filed on Feb. 16, 1989, now abandoned, which is a continuation of application No. 06/897,962, filed on Aug. 19, 1986, now abandoned.

(51) Int. Cl.[7] .................................................. A61K 9/14
(52) U.S. Cl. ........................................ 604/514; 604/522
(58) Field of Search ........................... 604/54, 58, 514, 604/522; 530/399, 351, 324–330; 514/12–18; 128/203.27, 200.22, 203.15, 200.14–200.23

(56) References Cited

U.S. PATENT DOCUMENTS

| 4,537,878 A | 8/1985 | Plotnikoff |
| 4,548,922 A | 10/1985 | Carey et al. |
| 4,590,003 A | 5/1986 | Twardzik et al. |
| 4,613,500 A | 9/1986 | Suzuki et al. |
| 4,628,045 A | 12/1986 | Hahn |
| 4,645,828 A | 2/1987 | Twardzik et al. |

(List continued on next page.)

FOREIGN PATENT DOCUMENTS

| AU | 4841285 | 10/1985 |
| EP | 0 124 243 A1 | 11/1984 |
| EP | 0 128 831 A2 | 12/1984 |

(List continued on next page.)

OTHER PUBLICATIONS

Illustrated Stedman's Medical Dictionary, 24th Ed., 1982, p. 29.
Byron, P.R., "Drug Development and Industrial Pharmacy," 12(7):993–1015 (1986).
Metcalf, D., *Nature* 339:27–30 (1989).
Nicola, N.A., *Annu. Rev. Biochem.* 58:45–77 (1989).
Vilcek, J., and Lee, T.H., *J. Biol. Chem.* 266:7313–7316 (1991).
Camussi, et al., *Eur. J. Biochem.* 202:3–14 (1991).
Wong and Goeddel, *Nature* 323:819 (1986).
Feduchi, et al. *J. Virol.* 63:1354 (1989).
Fiers, W., *Feb. Eur. Biochem. Soc.* 285:199–212 (1991).
Wigley et al., "Insulin Across Respiratory Mucosae by Aerosol Delivery", Diabetes, 20(8):552–556 (1971).
Mutch, "Inhalation of Chemotherapeutic Substances", The Lancet, Dec. 16, 1944 pp. 775–780.
Greenberg et al., "Prophylatic Effect of Low Doses of Human Leukocyte Interferon Against Infection with Rhinovirus", The Journal of Infectious Diseases, 145(4)542–546 (1982).
Sun et al., "Efficacy of Aerosolized Recombinant Interferons Against Vesicular Stomatitis Virus–Induced Lung Infection in Cotton Rats", Journal of Interferon Research, 4:449–454 (1984).

(List continued on next page.)

*Primary Examiner*—Mark Bockelman
(74) *Attorney, Agent, or Firm*—Flehr Hohbach Test Albritton & Herbert LLP (57) ABSTRACT

Polypeptides selected from the group of growth factors and cytokines are administered by intrapulmonary inhalation. Disclosed are novel compositions and devices for effecting the intrapulmonary administration of these polypeptides.

46 Claims, 4 Drawing Sheets

U.S. PATENT DOCUMENTS

| | | | |
|---|---|---|---|
| 4,699,136 A | 10/1987 | Krauser | |
| 4,710,305 A | 12/1987 | Zoltan et al. | |
| 4,746,508 A | 5/1988 | Carey et al. | |
| 4,771,769 A | 9/1988 | Hegemann et al. | |
| 4,860,738 A | 8/1989 | Hegemann et al. | |
| 4,959,358 A | 9/1990 | Carey et al. | |
| 5,082,658 A | 1/1992 | Palladino | |
| 5,284,656 A | 2/1994 | Platz et al. | |
| 5,354,934 A | 10/1994 | Pitt et al. | |
| 6,099,517 A | * | 8/2000 | Daugherty |

FOREIGN PATENT DOCUMENTS

| | | | |
|---|---|---|---|
| EP | 0 170 715 A1 | 2/1986 | |
| EP | 0 211 321 | 2/1987 | |
| JP | 60-161924 | 8/1985 | |

OTHER PUBLICATIONS

Wyde et al., "Pulmonary Deposition and Clearance of Aerosolized Interferon", Antimicrobial Agents and Chemotherapy, 25(6):729–734 (1984).

Wyde et al., "Duration of Effect of Interferon Aerosol Prophylaxis of Vesicular Stomatis Virus Infection in Mice", Antim. Agts. and Chemo., 27(1):60–64 (1985).

Sun et al., "Limited Efficacy of Aerosolized Recombinant Alpha Interferon against Virulent Influenze A/HK Infection in Mice (42257)", Proceedings of the Society for Experimental Biology and Medicine, 181:298–304 (1986).

Jia–Xiong et al., "Children's Respiratory Viral Diseases Treated with Interferon Aerosol", Chinese Medical Journal, 100(2):162–166 (1987).

Wyde et al., "Interferon Aerosol Suppression of Vesicular Stomatitis Virus Replication in the Lungs of Infected Mice", Antimicrobial Agents and Chemotherapy, 26(4):450–454 (1984).

Rudent et al., "Enhanced Resistance of Mice Against Influenza Virus Infection after Local Administration of Glycoprotein Extracts from Klebsiella Pneumoniae", Int. J. Immunopharmac. 7(4):525–531 (1985).

Mojard et al., "Differential Responses of Human Asthmatics to Inhaled Vasoactive Intestinal Peptide (VIP)", American Review of Respiratory Disease, 131(4):A281 (1985).

May, "The Collison Nebulizer:Description, Performance and Application", Aerosol Science, 4:235–243 (1973).

Devilbiss Health Care Inc. Catalogue, "Atomizers, Nebulizers, Powder Blowers, Syringes, Irrigators, Compressors."

Primagi et al., "Vaccination by the Aerosol Method", Erkrank Atom, –Org., 150:239–242 (1978).

Murray–Nadel, Textbook of Respiratory Medicine, Chapter 17: "Deposition and Clearance", W.B. Saunders & Co., (1988).

Egan, "Lung inflation, lung solute permeability, and alveolar edma", American Physiological Society, pp. 121–125 (1982).

Niewoehner, et al., "Injurios effects of lysophosphatidylcholine on barrier properties of alvolar epithelium", J. Appl. Physiol. 63(5) pp. 1979–1986 (1987).

Goren et al., "Differential permeability of endothelial and epithelial barriers to albumin flux", American Physiological Society, pp. 1315–1324 (1979).

Schneeberger–Keeley et al., The Ultrastructural Basis of Alveolar–Capillary Membrane Permeability to Peroxidase Used as a Tracer, The Journal of Cell Biology, 37:781–793 (1968).

Williams, "Endocytosis in alveolar type II cells:Effect of charge and size of tracers", Proc. Natl. Acad. Sci. USA, 81:6054–6058 (1984).

Taylor et al., "Permeability of the Alveolar Membrane to Solutes", Circulation Research, XVI:353–362 (1965).

Taylor et al., "Estimation of equivalent pore radii of pulmonary capillary and alveolar membranes", American Journal of Physiology, 218(4):1133–1140 (1970).

Kurzrock et al., "Phase I Study of Multiple Dose Intramuscularly Administered Recombinant Gamma Interferon", Journal of Clinical Oncology, 4(7):1101–1109 (1986).

Matsunaga et al., "Augmentation of In Vitro Cytotoxicity and In Vivo Tumor–Inhibition by Combined Use of Lymphotoxin–Containing Supernatants and Antitumor Drugs", Cancer Letters 20:21–28 (1983).

Neta et al., "Interleukin 1 is a Radioprotector", The Journal of Immunology, 136(7):2483–2485 (1986).

Staruch et al., "The Adjuvanticity of Interleukin 1 In Vivo", The Journal of Immunology, 130(5):2191–2194 (1983).

Nishimura et al., "Administration of slowly released recombinant interleukin 2—Augmentation of the efficacy of adoptive immunotherapy with lymphokine–activated killer (LAK) cells", Journal of Immunological Methods, 91:21–27 (1986).

Rosenberg et al., "A new approach to the therapy of cancer based on the systemic administration of autologous lymphokine–activated killer cells and recombinant interleukin–2", Surgery, 100(2):262–272 (1986).

Ettinghausen et al., "Immunotherapy of Murine Sarcomas Using Lymphokine Activated Killer Cells:Optimization of the Schedule and Route of Administration of Recombinant Interleukin–2", Cancer Research, 46:2784–2792 (1986).

Hubbell et al., "Antiproliferative and Immunodulatory Actions of .beta.–Interferon and Double–Stranded RNA, Individually and in Combination, on Human Bladder Tumor Xenografts in Nude Mice", Cancer Research, 45:2481–2486 (1985).

Preece et al., "Dose Dependence of Growth Response to Human Growth Hormone in Growth Hormone Deficiency", JCE & M, 42(3):477–483 (1976).

Gertner et al., "Prospective Clinical Trials of Human Growth Hormone in Short Children without Growth Hormone Deficiency", The Journal of Pediatrics, 104(2):172–176 (1984).

Rosenbloom et al., "Low Dose Single Weekly Injections of Growth Hormone: Response During First Year of Therapy of Hypopituitarism", Pediatrics, 66(2):272–276 (1980).

Hallworth et al., "A Comparison of the Regional Deposition in a Model Nose of a Drug Discharged from Metered Aerosol and Metered–Pump Nasal Delivery Systems", J. Allergy Clin. Immunol., 77:348 (1986).

Newman et al., "Deposition Pattern from a Nasal Spray Pump", Rhinology, 25:77 (1987).

Newman et al., "The Nasal Distribution of Metered Dose Inhalers", J. Laryngol. Otol., 101:127 (1987).

Hardy et al., "Intranasal Drug Delivery by Sprays and Drops", J. Pharm. Pharmacol., 37:294 (1985).

Bensch et al., Absorption of Intact Protein Molecules across the Pulmonary Air–Tissue Barrier, Science, vol. 157, pp. 1204–1206 (1967).

Bensch et al., Studies on the Pulmonary Air–Tissue Barrier; Part IV: Cytochemical Trancing of Macromolecules during Adsorption, Yale J. Biol. Med., vol. 43, pp. 236–241 (1971).

Scheeberger et al., Structural Basis for Some Permeability Properties of the Air–Blood Barrier, Fed. Proc. vol. 37(11), p. 2471 (1978).

Padmanabhan et al., Protection Against Pulmonary Oxygen Toxicity in Rats by the Intratracheal Administration of Liposome–Encapsulated Superoxide Dismutase of Catalase, Am. Rev. Respir. Dis., vol. 132(10, pp. 164–167 (1985).

Richardson et al., Uptake and Transport of Exogenous Proteins by Respiratory Epithelium, Lab. Invest., vol. 35(4), p. 307 (1976).

Diviskas et al., *J. Appl. Physiol.* 69:362–372 (1990).

Illum, "Nasal Delivery of Peptides, Factors Affecting Nasal Absorption," *Topics in Pharmaceutical Science* (eds. Crommelin and Midha), Medpharm Scientific Publishers, Stuttgart, Chap. 5 (1992).

Disanto in *Reminton's Pharmaceutical Sciences* (ed. Gennero et al.), 17th ed., chap. 77, (1985).

Debs et al., *J. Immunology* 140:3482–3488 (1988).

Niven et al. *J. Controlled Release* 32:177–189 (1994).

Patton et al. *J. Controlled Release* 28:79–85 (1994).

Braquet et al., *J. Cardiovasc. Pharmacol.* 13(Supp. 5):S143–146 (1989) (Abstract).

* cited by examiner

Fig.1.

INTRAPULMONARY DELIVERY OF POLYPEPTIDE GROWTH FACTORS AND CYTOKINES

This is a continuation of application Ser. No. 08/128,058 filed Sep. 27, 1993 now U.S. Pat. No. 6,099,517, which is a continuation of application Ser. No. 07/982,268, filed Nov. 25, 1992 abandoned, which is a continuation of application Ser. No. 07/762,039 filed Sep. 17, 1991 abandoned, which is a continuation of application Ser. No. 07/312,325 filed on Feb. 16, 1989 abandoned, which is a continuation of application Ser. No. 06/897,962 filed Aug. 19, 1986 abandoned.

This invention relates to the administration of proteins by adsorption from the lungs. In particular, it is concerned with providing therapeutic, sustained doses of growth hormones or cytokines to the bloodstream without irritating or otherwise damaging lung tissue.

Drug delivery by pulmonary absorption from particles such as aerosols has met with considerable success in several instances of localized delivery to lungs as the drug target tissue, most notably the use of beta adrenergic antagonists in the treatment of asthma. Other drugs that have been administered in this fashion include corticosteroids and cromolyn sodium. On the other hand, the administration of aminoglycoside antibiotics, antiviral drugs and anti-cancer drugs for systemic action by this route has only met with spotty success. In some cases, lack of delivery to the blood stream was attributed to inability of the drug to pass through the alveolar epithelium. In other cases the drug was found to be irritating and bronchoconstrictive (Juliano, 1984, "Pharm. Ther.", 24:355–365). At this time it is not possible to reasonably predict in advance that any given drug will be nonirritating or will be adsorbed through the lungs in an amount sufficient to be therapeutically useful.

Similarly, extensive studies have been conducted on the pulmonary absorption of proteins and polypeptides. While size, lipophobicity, and possibly other poorly characterized features of such molecules appear to create a substantial barrier to their absorption into the blood stream (Juliano, op cit; Egan, 1983, "Am. Rev. Resp. Dis." 127(5) Pt. 2 537–539; Hogg et al., 1979, "Fed. Proc." 38(2):197–201), there remains considerable disagreement about protein permeability from the alveoli into the blood under ordinary conditions. For example, studies with albumin or horse radish peroxidase (HRP) are illustrative.

Dominguez et al. ("Lab. Invest." 16(6):905 [1967]) observe that the alveolar wall is only "slightly permeable" to albumin. Similarly, earlier workers found no pulmonary absorption of homologous plasma albumin at all (Drinker et al., 1947 "J. Exp. Med." 86:7), while other demonstrated absorption of albumin only from lung subsections hyperinflated in excess of 40 cm $H_2O$ pressure; the same pressure applied to the total lung did not produce protein permeability (Egan et al., 1982, "J. Appl. Physiol." 53:121). Newborn lambs were found to be capable of pulmonary albumin absorption, but only for a brief period postpartum (Egan et al., 1984, "Ped. Res." 18(6):566). Finally, Bensch et al. ("Science" 157:1204–1206 [1967]) report the rapid absorption of instilled solutions of radioactively labelled albumin or gamma globulin across the pulmonary air-tissue barrier. More than two thirds of the administered polypeptides could be accounted for in the blood of the test animals after 24 hours. These authors also report the work of others (Drinker et al., op cit) to the effect that removal of lower molecular weight proteins from the lumin of the alveoli occurs only after degradation of the molecules, notwithstanding that Bensch et al. did not detect degradation of albumin or gamma globulin.

Bensch et al. ("Yale J. Biol. Med." 43:236–241 [1971]) later observed (based on similar studies with HRP) that macromolecules may cross the air-blood barrier by being transported directly into the pulmonary capillary blood in the pinocytotic vesicles of the membranous pneumocyte and endothelial cells. However, the Bensch et al. experiments were conducted by instilling HRP into the lungs in the form of an aqueous solution.

Conner et al. ("Fundamental and Appl. Toxicology" 5:99–104 [1985]) instilled a solution of HRP into the trachea of experimental animals after exposure to zinc oxide particles, suggesting that absorption of this protein was a function of pathological effects by zinc oxide. This was consistent with the report by Hogg et al., op cit. that the bronchial epithelium is normally nonpermeable to proteins unless damaged in some way, such as by cigarette smoke, ether, antigens, histamine, or methacholine.

Other polypeptide probes besides albumin, gamma globulin and HRP have been used in the study of pulmonary absorption. These include microperoxidase, equine cytochrome c, equine myoglobin, bovine lactoperoxidase and human myeloperoxidase (Schneeberger, 1978, "Fed. Proc." 37(11):2471), superoxide dismutase or catalase (Padmanabhan et al., 1985, "Am. Rev. Respir. Dis." 132 (1):164–167), and ferritin (Richardson et al., 1976, "Lab. Invest." 35(4):307). None of these agents, however, has been employed in a systemic therapeutic context, i.e. delivered in the expectation of achieving a therapeutic dosage at a desired site distal from the lungs per se.

U.S. Pat. No. 4,476,116 proposes delivering human growth hormone or interferon by intranasal absorption of a nasal spray containing the protein and a chelating agent. Since particles of 5 mm or greater are removed in the nasopharyngeal region (Juliano et al.) it must be concluded that an effective nasal spray would contain aerosol particles having at least this mean diameter. Similarly, EP 122036 describes a powdered composition for intranasal administration of growth hormone or interferon wherein at least 90% of the particles had an effective diameter of 10 to 250 microns. The minimum diameter was established with the object to avoid introducing the particles into the lungs.

Intranasal administration of growth hormone or interferons is undesirable because of dosage variability, side effects such as nasal irritation, extremely poor polypeptide permeability into the blood stream and polypeptide degradation by normal nasal microorganisms. Of course, these polypeptides have been conventionally administered by injection or infusion. This delivery route suffers from obvious deficiencies, the most glaring being the requirement for regular growth hormone injections in children or, in the case of interferons being employed for the treatment of malignancies, an absence of a healthy vasculature for catheterization of the patients. An improved method for the administration of these proteins is needed.

Accordingly, it is an object herein to obviate the need for injections or infusions of certain polypeptides.

It is a further object herein to reduce the frequency of administration of certain polypeptides by providing sustained release from pulmonary tissue.

It is another object to deliver therapeutically effective doses of certain polypeptides without therapeutically significant degradation of the polypeptides or the use of agents that lead to irritation of the bronchi, epithelium or other pulmonary tissue.

These and other objects of the invention will be apparent to the ordinary artisan from the specification as a whole.

SUMMARY

The foregoing objects are accomplished by providing a method for delivering to the blood stream of a patient a therapeutic dose of a polypeptide selected from the group of growth factors and cytokines, which method comprises delivering a therapeutically effective dose of the polypeptide into the lungs of the patients. A device is provided for accomplishing this method that comprises reservoir means for storing the polypeptide; a therapeutic dosage form of the polypeptide disposed in the reservoir means; dispersing means for forming in a gas a suspension of particles comprising the polypeptide wherein the size of the particles is sufficiently small to permit their penetration into the alveoli of the patient's lungs upon inhalation; means for transporting the polypeptide to the dispersing means; and means for delivering the particle suspension to alveoli of the patient's lungs.

An advantage with respect to the delivery of therapeutic doses of these particular polypeptides is that they are delivered systemically by pulmonary absorption without pathological effects on the lungs or a requirement for an epithelial irritant or absorption enhancing agent such as ether, zinc oxide, antigens, histamine, methacholine, water soluble amphophilic steroids, bile salts such as sodium glycocholate, lower alkyl ethers of cellulose, chelating agents or water absorbing-water insoluble substances such as polyvinyl pyrrolidone, sodium carboxymethyl cellulose, polyacrylates and the like.

DETAILED DESCRIPTION

The polypeptides to be delivered by intrapulmonary absorption are growth factors and cytokines. Growth factors or hormones are polypeptides that induce the proliferation or enlargement of target cells. Such factors or hormones, hereafter referred to as hormones for convenience, may incidentally increase the respiratory rate or metabolism of the target cells, but in the absence of increased cell mitosis or enlargement a polypeptide is not to be considered a growth hormone for the purposes of this application. Most growth hormones exhibit a molecular weight of about from 5 kD to 75 kD and a pI ranging from about 4 to 8. Specific examples include growth hormone (somatropin), thymosin, somatomedins such as IGF-1 or IGF-2, transforming growth factors-a and b, nerve growth factor, platelet-derived growth factor, ovarian growth factor, fibroblast growth factor, myoblast growth factor, epidermal growth factor and the like, but excluding insulin. These substances are well known to those skilled in the art and, in many cases, have been cloned and expressed in recombinant organisms. The preferred growth hormone for use herein is somatropin or its N-terminal methionylated variant (somatrem) described below.

Cytokines are the polypeptide secretory products of cells constituting the immune system, e.g. lymphocytes such as B-cells and T cells, including helper and suppressor T cells, macrophages and neutrophils. Cytokines serve as effectors in that they induce changes in the activity or secretory products of other immune cells, or as direct acting proteins in that they induce a change in a target non-immune cell. Furthermore, many cytokines, e.g. thymosin or gamma interferon, may be considered growth hormones as well in that they induce the proliferation of specialized immune target cells. Typically, cytokines have molecular weights of about from 5 kD to 30 kD and pI of about from 4 to 8. Examples of cytokines include the interleukins, tumor necrosis factors, interferons and immune suppressor factors. Preferred cytokines for use herein are tumor necrosis factors-a and b, the interferons-a, b and g.

The terms growth hormone and cytokine are to be considered to include amino acid sequence, glycosylation and other variants of the native molecules. These variants may exhibit enhanced levels of the normal biological activity of the native molecules or may, on the contrary, act antagonistically towards the native molecule. Alternatively, variants are selected for improved characteristics such as stability to oxidation, extended biological half-life, and the like. Such variants as are known or will be developed in the future are suitable for use herein. For example, N-terminal methionyl human growth hormone (somatrem) is an example of a common variant produced in recombinant cell culture wherein a methionine residue not found in the native analogue is covalently bound to the normal N-terminal amino acid residue.

The polypeptides administered in accordance with this invention are first placed into a particulate dispersed form. This is accomplished by preparing an aqueous aerosol or solid particles which contain the polypeptide. Ordinarily, an aqueous aerosol is made by formulating an aqueous solution or suspension of the desired polypeptide together with conventional pharmaceutically acceptable carriers and stabilizers. The carriers and stabilizers will vary depending upon the requirements for each polypeptide, but typically include nonionic surfactants (Tweens, Pluronics or polyethylene glycol), innocuous proteins like serum albumin, sorbitan esters, oleic acid, lecithin, amino acids such as glycine, buffers, salts, sugars or sugar alcohols. The formulations also can include mucolytic agents such as those described in U.S. Pat. No. 4,132,803, as well as bronchodilating agents. The formulations will be sterile. Aerosols generally will be prepared from isotonic solutions. The particles optionally include normal lung surfactant proteins.

It is within the scope of this invention to form aerosols of particles in aqueous or nonaqueous, e.g. fluorocarbon propellant, suspension. Such particles include, for example, intramolecular aggregates of the polypeptides or liposomal or microcapsular-entrapped polypeptides. The aerosols should be free of lung irritants, i.e. substances which cause acute bronchoconstriction, coughing, pulmonary edema or tissue destruction. However, nonirritating absorption enhancing agents are suitable for use herein.

Sonic nebulizers preferably are used in preparing aerosols. Sonic nebulizers minimize exposing the polypeptides to shear, which can result in degradation of the molecule. A suitable device is the Bird Micronebulizer. However, it is also within the scope of this invention to employ other atomizing or nebulizing systems or intratracheal delivery systems, e.g. U.S. Pat. No. 3,915,165, the aerosol generator-inhalator described in EP 166476 the jet nebulizers described by Newman et al. "Thorax" 40(9):671–676 (1985), metered dose inhalers (M. Berenberg, 1985, "J. Astham-USA" 22(2):87–92), or other devices (Sears et al., 1983 "N.Z. Med. J." 96:643II; O'Reilly et al., 1983, "Br.

Med. J." 286:6377; or J. Stander et al., 1982, "Respiration" 44(3):237–240), so long as they are compatible with the protein to be administered and are capable of delivering particles of the desired size.

Particulate aerosol suspensions are essentially fine dry powders containing the polypeptides. They are prepared by any number of conventional procedures. The simplest method of producing them is to micronize polypeptide, e.g. crystals or lyophilization cakes, and suspend the particles in dry fluorocarbon propellants. In these formulations the polypeptides do not dissolve in the hydrophobic propellants (which evaporate after the suspension is released from the pressurized device into the air). Rather, the polypeptides are suspended in the fluorocarbon. In an alternate embodiment the polypeptides are stored in a compartment separate from the propellant. Discharge of the propellant withdraws a predetermined dose from the storage compartment. The devices used to deliver drugs in this manner are known as metered dose inhalers (MDIs) (P. R. Byron, 1986, "Drug Development and Industrial Pharmacy" 12:993).

The size of the aerosols or particles generally will range about from 0.5 mm to 4 mm, preferably about 0.5 to 1 mm. Smaller particles are less acceptable because they tend not to be deposited but instead are exhaled. Larger particles are not preferred because in large measure are unable to be deposited at the level of the alveoli, being removed by impaction within the nasopharyngeal or oral cavities (Byron, 1986, "J. Pharm. Sci." 75:433). Obviously, most aerosol or particulate compositions will be heterogenous in size distribution, although heterogeneity can be reduced by known methods, e.g. the screening unit described in EP 135390A. Heterogeneity will not be disadvantageous unless the proportion of particles having an average means diameter in excess of about 4 mm is so large as to impair the delivery of the therapeutic dose by pulmonary inhalation. Suspensions containing greater than about 15% of particles within the 0.5–4 mm range can be used, but generally the proportion of particles having an average mean diameter larger than 4 mm should be less than about 25%, and preferably not greater than 10%, of the total number of particles. The diameters recited refer to the particle diameters as introduced into the respiratory tract.

The particles may or may not bear a net charge. The presence of a net charge is desirable for minimizing particle aggregation in the airways since the particles will repel one another electrostatically. Charged particles are made by removing water from solutions of the polypeptides at a pH other than the isoelectric point, e.g. ordinarily about from 0.5 to 2 pH units on either side of the isoelectric point. On the other hand, dewatering of polypeptides at a pH other than the isoelectric point may result in precipitation or denaturation of the protein, so the desirability of use of such a pH will depend upon the known characteristics of the polypeptide to be administered.

Figure 1:
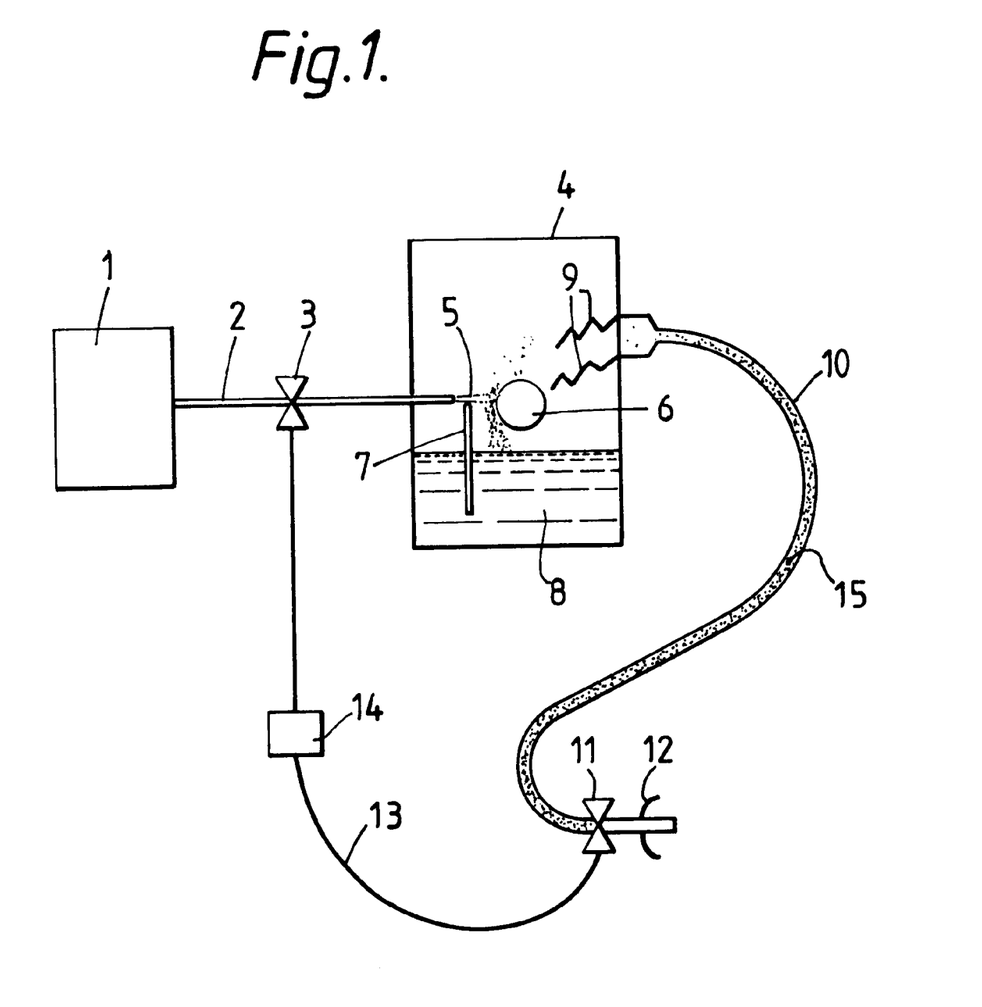
FIG. 1 is a schematic depiction of a device for intrapulmonary delivery of a polypeptide aerosol.

A suitable system for inhalation delivery of the polypeptides herein is illustrated in FIG. 1. A source of compressed air 1 communicates with a nebulizer shown generally at 4 by way of a conduit 2. The flow of compressed air is controlled by valve 3. The nebulizer 4 contains a capillary tube 7 which extends down into the solution of growth hormone or cytokine in reservoir 8. The end of capillary 7 which is distal to solution reservoir 8 terminates immediately adjacent to the orifice 5 of conduit 2. An impaction sphere 6 is adjustably positioned opposite orifice 5. The orifice 5, capillary 7 and sphere 6 serve as the dispersing means for forming the aerosol of the polypeptide disposed in reservoir 8. Nebulizer 4 also includes serrated output baffles shown generally at 9, downstream of which is a conduit 10 communicating with a respirator mouthpiece 12 for sealably engaging the mouth of the patient (not shown). The passage of aerosol 15 through conduit 10 is controlled by valve 11, which also operates valve 3 through circuit 13 and control device 14.

In operation, compressed air is valved by valve 3 on demand as determined by programmed control device 14. The control device is actuated on demand from valve 11. Compressed air passes through conduit 2 and out the orifice 5. The flow of air over the end of capillary 7 draws the solution of polypeptide from reservoir 8 into the stream of air where, together with collision on the impaction sphere 6, an aerosol of the solution is formed. The stable aerosol suspension is forced out by air pressure through baffles 9 and down conduit 10 upon demand from valve 11 as activated by the patient. The baffles are selected on appropriate size, dimension and composition to remove the bulk of particles greater than about 4 mm. The seating of mouthpiece 12 will ensure that the patient inhales substantially only the delivered mixture of air and aerosolized polypeptide with each breath.

The method herein is illustrated by way of the following examples, which are not to be construed as limiting the invention.

EXAMPLE 1

Intrapulmonary Delivery of met-hGH

Figure 2:
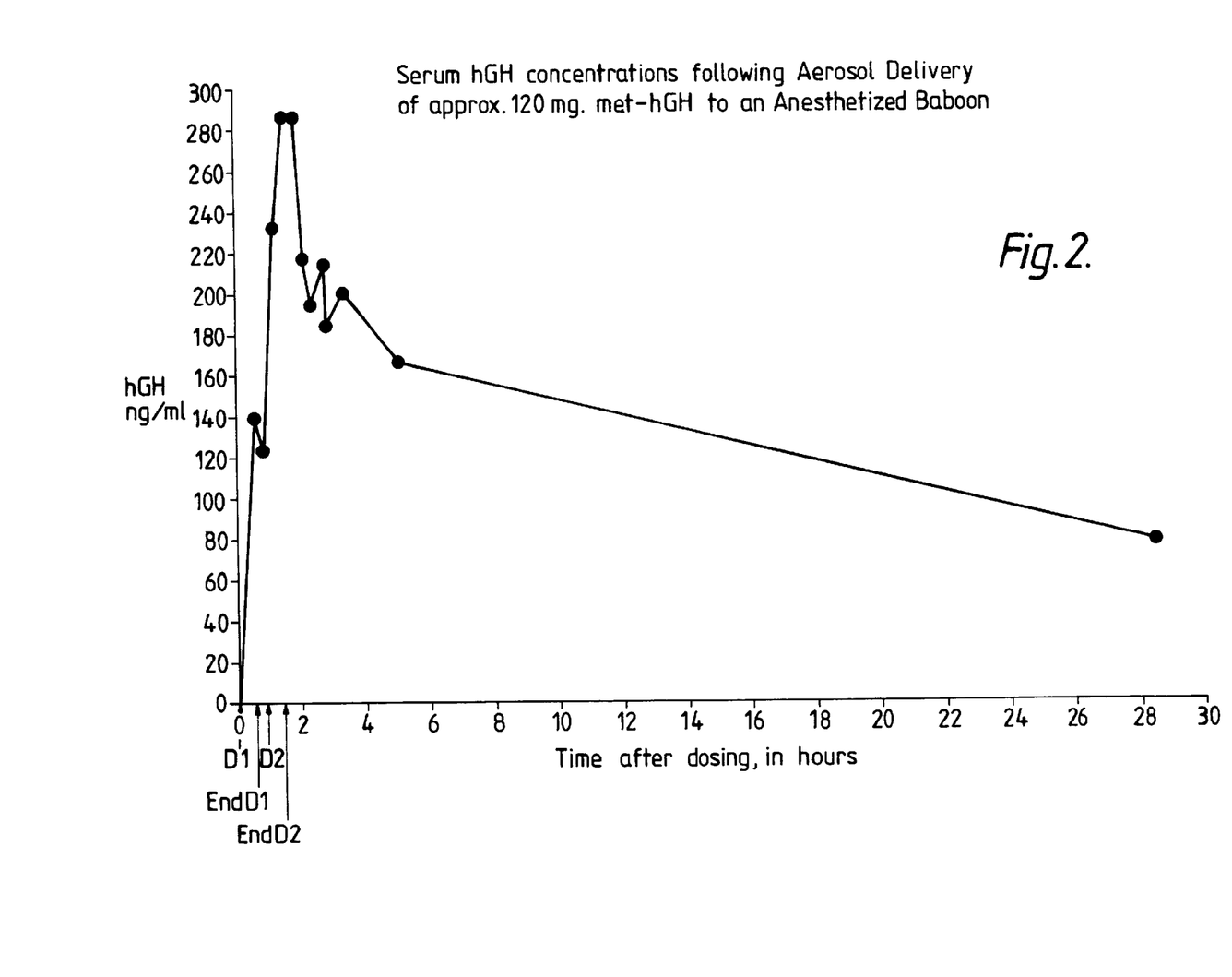
FIG. 2 depicts the serum hGH concentrations following fine aerosol intrapulmonary delivery of methionyl human growth hormone to an anesthetized baboon. Two doses of 60 mg each are shown as D1 and D2. Each dosing was terminated at the points designated "End D1" and "End D2". Serum growth hormone concentrations increased rapidly and additively after each administration.

An adult baboon weighing 24 kg was anesthetized with intravenous pentobarbital, a tracheal intubation performed and the animal allowed to breathe normally until and between dosing. A Bird Micronebulizer in line with a Bird Mark 7 respirator was charged with 5–10 ml of a solution of 12 mg/ml Protropin$^R$ brand of met-hGH (somatrem) in mannitol/phosphate buffer. The Micronebulizer then was used to simultaneously ventilate and dose the animal at 22 cm $H_2O$ at a rate of 1.8 mg/hGH/-min. for 30 min. At this pressure the animal ventilated at approximately normal inspiratory volume. The animal was allowed to exhale normally after each ventilated breath and was positioned supine for dosing. After the first dosing period the animal was allowed to breathe normally for another 20 minutes, after which a second dosing was performed in the same way as the first. Blood plasma samples were taken at the initiation time of the first dose and thereafter as shown by the data points in FIG. 2. The baboon completely emerged from anesthesia 8 hours after the last pentobarbital injection. Radioimmunoassays of met-hGH in these sera showed that intrapulmonary delivery in accord herewith produced a blood level that is greater than twice that which is considered an acceptable therapeutic dose when administered intramuscularly. The radioimmunoassay employed in this example also will cross-react with normal baboon growth hormone, so it is believed that some of the hGH detected at 28 hours after the commencement of dosing may represent a circadian or stress induced increase in baboon growth hormone, probably similar to the levels in rhesus monkeys (10 ng/ml). Since the normal detectable GH levels in primates typically fall within the 10–20 mg/ml range, the method of this invention made is possible to deliver far in excess of a systemic therapeutically effective dose of hGH for a period exceeding 28 hours. This was particularly surprising since the general view is that long term drug delivery (>12 hr) is not achievable by intrapulmonary inhalation (Byron, op cit.).

EXAMPLE 2

Intratracheal Instillation of Interferon or Tumor Necrosis Factor

Figure 3:
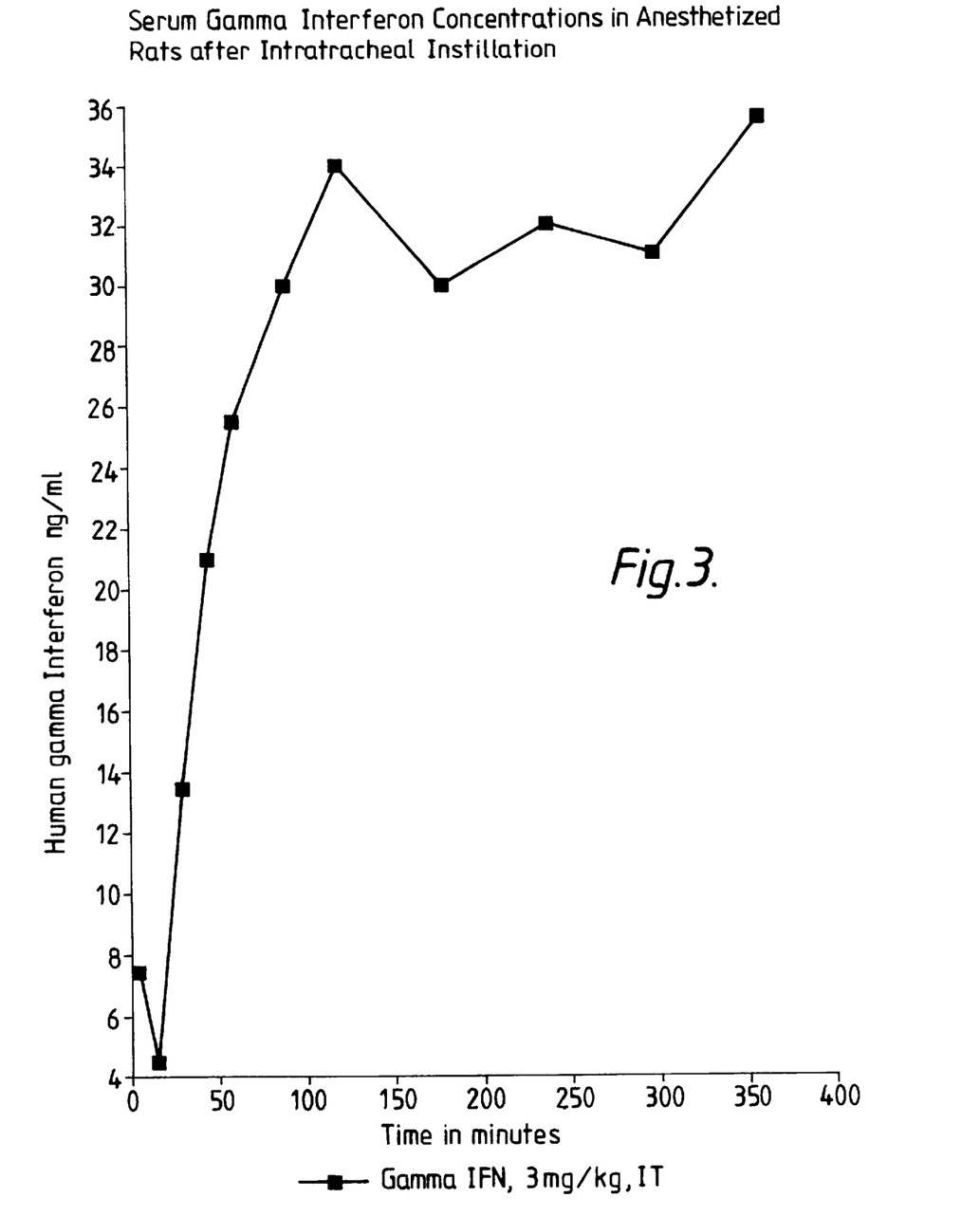
FIGS. 3 and 4 show the serum concentrations of human gamma interferon and tumor necrosis factor-a after intratracheal instillation thereof into anesthetized rats. The intratracheal dose is shown below each group.
Figure 4:
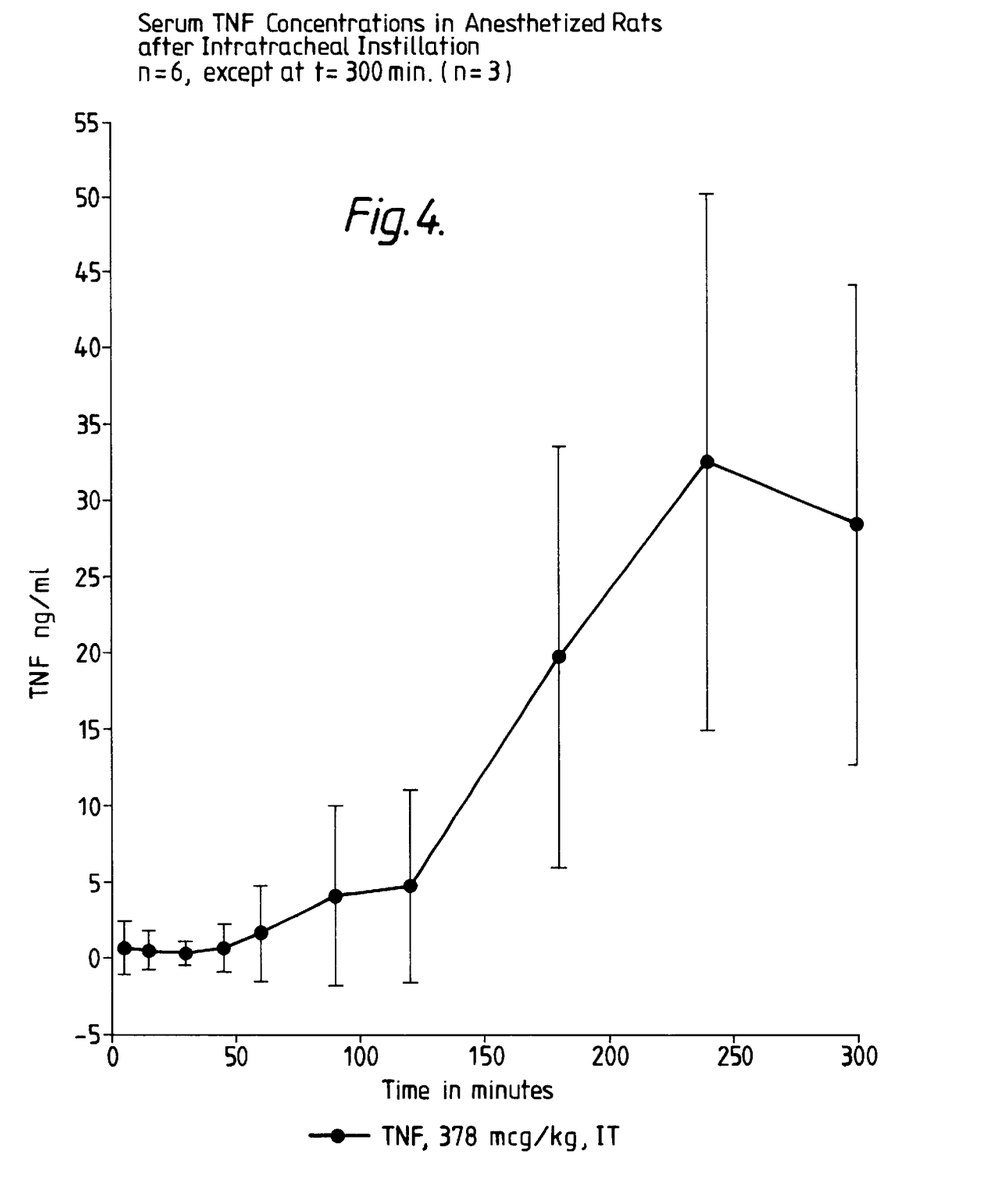

Adult rats were anesthetized and tracheal intubations performed on each animal. Solutions of human recombinant gamma interferon and human recombinant tumor necrosis factor were injected into the trachea of test animals until a dosage of 3 mg/Kg and 378 mcg/Kg, respectively, was delivered. Serum samples were withdrawn from each test animal at the times indicated in FIGS. 3–4 and assayed for the appropriate polypeptide. The results, shown in FIGS. 3–4, clearly demonstrate effective system delivery of these two cytokines.

What is claimed is:

1. A method for sustained systemic delivery to a patient a therapeutically effective dose of a therapeutically active growth factor having a molecular weight of about 5 to 75 kD, said method comprising administering to said patient by inhalation, aerosol or solid particles comprising said growth factor, wherein said particles are unaccompanied by an absorption enhancing agent and are sufficiently small to permit their penetration into the alveoli of the lung such that said growth factor is delivered systemically by pulmonary absorption in an amount effective to raise blood level concentrations to a therapeutically effective level over a sustained period of time.

2. The method of claim 1 wherein the growth factor is present in particulates greater than about 15% of which have a diameter of about 0.5 to 4 μm.

3. The method of claim 1 wherein said growth factor is delivered into the alveoli of the lungs without substantial contact with the nasal passages.

4. The method of claim 1 wherein the growth factor is delivered by the blood stream to a site distal from the lungs.

5. The method of claim 1 wherein said aerosol is an aqueous aerosol.

6. The method of claim 1, wherein said growth factor is selected from the group consisting of growth hormone, thymosin, IGF-1, IGF-2, transforming growth factor (TGF)-a, TGF-b, nerve growth factor, platelet-derived growth factor, ovarian growth factor, epidermal growth factor and gamma interferon.

7. The method of claim 6 wherein said growth factor is a human growth hormone.

8. The method of claim 7 wherein said human growth hormone is somatropin.

9. The method of claim 7 wherein said human growth hormone is sometrem.

10. The method of claim 1, wherein said sustained period is greater than 5 hours.

11. The method of claim 10, wherein said sustained period is greater than 28 hours.

12. The method for sustained systemic delivery to a patient of a therapeutically active human growth hormone having a molecular weight of about 5 to 75 kD, said method comprising administering to said patient by inhalation, aerosol or solid particles comprising said growth hormone, wherein said particles are unaccompanied by an absorption enhancing agent and are sufficiently small to permit their penetration into the alveoli of the lung such that said growth hormone is delivered systemically by pulmonary absorption in an amount effective to raise blood level concentrations to a therapeutically effective level over a sustained period of time.

13. The method of claim 12 wherein the growth hormone is present in particulates greater than about 15% of which have a diameter of about from 0.5 to 4 μm.

14. The method of claim 12 wherein said growth hormone is delivered into the alveoli of the lungs without substantial contact with the nasal passages.

15. The method of claim 12 wherein the growth hormone is delivered by the blood stream to a site distal from the lungs.

16. The method of claim 12 wherein said aerosol is an aqueous aerosol.

17. The method of claim 12 wherein said sustained period is greater than 5 hours.

18. The method of claim 17, wherein said sustained period is greater than 28 hours.

19. A method for sustained systemic delivery to a patient of somatropin, said method comprising administering to said patient by inhalation, aerosol or solid particles comprising said somatropin, wherein said particles are unaccompanied by an absorption enhancing agent and are sufficiently small to permit their penetration into the alveoli of the lung such that said somatropin is delivered systemically by pulmonary absorption in an amount effective to raise blood level concentrations to a therapeutically effective level over a sustained period of time.

20. The method of claim 19 wherein the somatropin is present in particulates greater than about 15% of which have a diameter of about from 0.5 to 4 μm.

21. The method of claim 19 wherein said somatropin is delivered into the alveoli of the lungs without substantial contact with the nasal passages.

22. The method of claim 19 wherein th somatropin is delivered by the blood stream to a site distal from the lungs.

23. The method of claim 19 wherein said aerosol is an aqueous aerosol.

24. The method of claim 19, wherein said sustained period is greater than 5 hours.

25. The method of claim 24, wherein said sustained period is greater than 28 hours.

26. A method for sustained systemic delivery to a patient of somatrem, said method comprising administering to said patient by inhalation, aerosol or solid particles comprising said somatrem, wherein said particles are unaccompanied by an absorption enhancing agent and are sufficiently small to permit their penetration into the alveoli of the lung such that said somatropin is delivered systemically by pulmonary absorption in an amount effective to raise blood level concentrations to a therapeutically effective level over a sustained period of time.

27. The method of claim 26 wherein the somatrem is present in particulates greater than about 15% of which have a diameter of about from 0.5 to 4 μm.

28. The method of claim 26 wherein said somatrem is delivered into the alveoli of the lungs without substantial contact with the nasal passages.

29. The method of claim 26 wherein the somatrem is delivered by the blood stream to a site distal from the lungs.

30. The method of claim 26 wherein said aerosol is an aqueous aerosol.

31. The method of claim 26, wherein said sustained period is greater than 5 hours.

32. The method of claim 31, wherein said sustained period is greater than 28 hours.

33. A method for sustained systemic delivery to a patient of a gamma interferon having a molecular weight of about 5 to 30 kD, said method comprising administering to said patient by inhalation, aerosol or solid particles comprising said gamma interferon, wherein said particles are unaccompanied by an absorption enhancing agent and are sufficiently small to permit their penetration into the alveoli of the lung such that said gamma interferon is delivered systemically by pulmonary absorption in an amount effective to raise blood level concentrations to a therapeutically effective level over a sustained period of time.

34. The method of claim 33 wherein the gamma interferon is present in particulates greater than about 15% of which have a diameter of about from 0.5 to 4 μm.

35. The method of claim 33 wherein said gamma interferon is delivered into the alveoli of the lungs without substantial contact with the nasal passages.

36. The method of claim 33 wherein the gamma interferon is delivered by the blood stream to a site distal from the lungs.

37. The method of claim 33 wherein said aerosol is an aqueous aerosol.

38. The method of claim 33, wherein said sustained period is greater than 5 hours.

39. The method of claim 38, wherein said sustained period is greater than 28 hours.

40. A method for sustained systemic delivery to a patient of tumor-necrosis factor-α having a molecular weight of about 5 to 30 kD, said method comprising administering to said patient by inhalation, aerosol or solid particles comprising said tumor-necrosis factor-α, wherein said particles are unaccompanied by an absorption enhancing agent and are sufficiently small to permit their penetration into the alveoli of the lungs such that said tumor-necrosis factor-α is delivered systemically by pulmonary absorption in an amount effective to raise said blood level concentrations to a therapeutically effective level over a sustained period of time.

41. The method of claim 40 wherein the tumor-necrosis factor-α is present in particulates greater than 15% of which have a diameter of about from 0.5 to 4 μm.

42. The method of claim 40 wherein said tumor-necrosis factor-α is delivered into the alveoli of the lungs without substantial contact with the nasal passages.

43. The method of claim 40 wherein the tumor-necrosis factor-α is delivered by the blood stream to a site distal from the lungs.

44. The method of claim 40 wherein said aerosol is an aqueous aerosol.

45. The method of claim 40, wherein said sustained period is greater than 5 hours.

46. The method of claim 45, wherein said sustained period is greater than 28 hours.

* * * * *